US00PP32437P2

(12) United States Plant Patent
Doyle

(10) Patent No.: US PP32,437 P2
(45) Date of Patent: Nov. 10, 2020

(54) FIG TREE NAMED '4-19'

(50) Latin Name: *Ficus carica*
Varietal Denomination: 4-19

(71) Applicant: James Doyle, Clovis, CA (US)

(72) Inventor: James Doyle, Clovis, CA (US)

( * ) Notice: Subject to any disclaimer, the term of this patent is extended or adjusted under 35 U.S.C. 154(b) by 0 days.

(21) Appl. No.: 16/602,686

(22) Filed: Nov. 19, 2019

(51) Int. Cl.
*A01H 5/08* (2018.01)
*A01H 6/00* (2018.01)

(52) U.S. Cl.
USPC ..... Plt./211

(58) Field of Classification Search
USPC ..... Plt./211
CPC ..... A01H 5/08; A01H 6/00
See application file for complete search history.

*Primary Examiner* — Keith O. Robinson
(74) *Attorney, Agent, or Firm* — Marcus N. DiBuduo; John R. Aaron

(57) ABSTRACT

A new and distinct variety of fig (*Ficus carica*) tree named '4-19', characterized by its large size and dark purple skin, as well as its productivity and regular bearing. The tree produces two crops, both the breba first crop and the productive second, or main, crop. The fruit eye is usually small, the fruit skin and meat are moderately thick and durable, and the fruit pulp has an attractive reddish color, is fine-textured, and is sweet and rich in flavor. The fruit appears to hold its size later into the season than other commercial varieties of figs, thus extending the season for prime size and quality figs.

4 Drawing Sheets

Latin name: *Ficus carica.*
Variety denomination: '4-19'.

BACKGROUND OF THE INVENTION

The present invention relates to a new and distinct cultivar of *Ficus* tree, botanically known as *Ficus carica* and hereinafter referred to by the name '4-19'.

The new fig selection, '4-19', originated from a controlled hybridization made in early summer of 2011 by the Inventor in Roseville, Calif. The parentage of this new selection is made up of two proprietary parents, the female (fig) parent 'SSB-121' (unpatented) and the male (caprifig) pollen parent 'G-88' (unpatented). Both parents are the property of the Inventor. 'SSB-121' is an open-pollinated seedling derived from seed of a black Smyrna type fig (unpatented). The caprifig 'G-88' is derived from a cross of the California Brown Turkey fig (unpatented), with the 'D3-11' caprifig (unpatented), a proprietary caprifig belonging to the Inventor. 'D3-11' has a genome derived primarily from the Calimyrna fig variety.

The new '4-19' selection was first asexually propagated by the Inventor during the 2015 growing season in Roseville, Calif., by taking cuttings from the original tree. The first propagule was planted by the Inventor in 2015 at a testing location controlled by the Inventor located near the town of Wilton in Sacramento County, Calif. (hereinafter referred to as the "Wilton" location). This propagated tree first produced a small amount of fruit at the Wilton location in 2017. Propagules of the original '4-19' seedling have shown that the unique features are stable and reproduced true to type.

SUMMARY OF THE INVENTION

The new '4-19' fig is of the common type and, thus, does not need to be pollinated to set and mature a crop of both breba and second crop fruit. The '4-19' fig is a large, dark purple-skinned fig and is characterized by a large tree that is productive and a regular bearer. The tree produces two crops—the first, or breba, crop and the productive second, or main, crop. The fruit eye of '4-19' is usually small, thereby restricting the entry of insects that could enter the fruit and cause internal decay. The fruit skin and meat are moderately thick and durable, making the fruit very suitable for packing and shipping as a fresh market product. The fruit pulp has an attractive reddish color, is fine-textured, and is sweet and rich in flavor. The fruit appears to hold its size later into the season than other commercial varieties of figs, thus extending the season for prime size and quality figs.

BRIEF DESCRIPTION OF THE PHOTOGRAPHS

The colors in the accompanying photographs are as nearly true as is reasonably possible in color photographs of this type. However, due to development, processing, printing, and reproduction, the leaves and fruit depicted herein may or may not be accurate when compared with the actual botanical specimens.

DETAILED BOTANICAL DESCRIPTION OF THE PLANT

Figure 1:
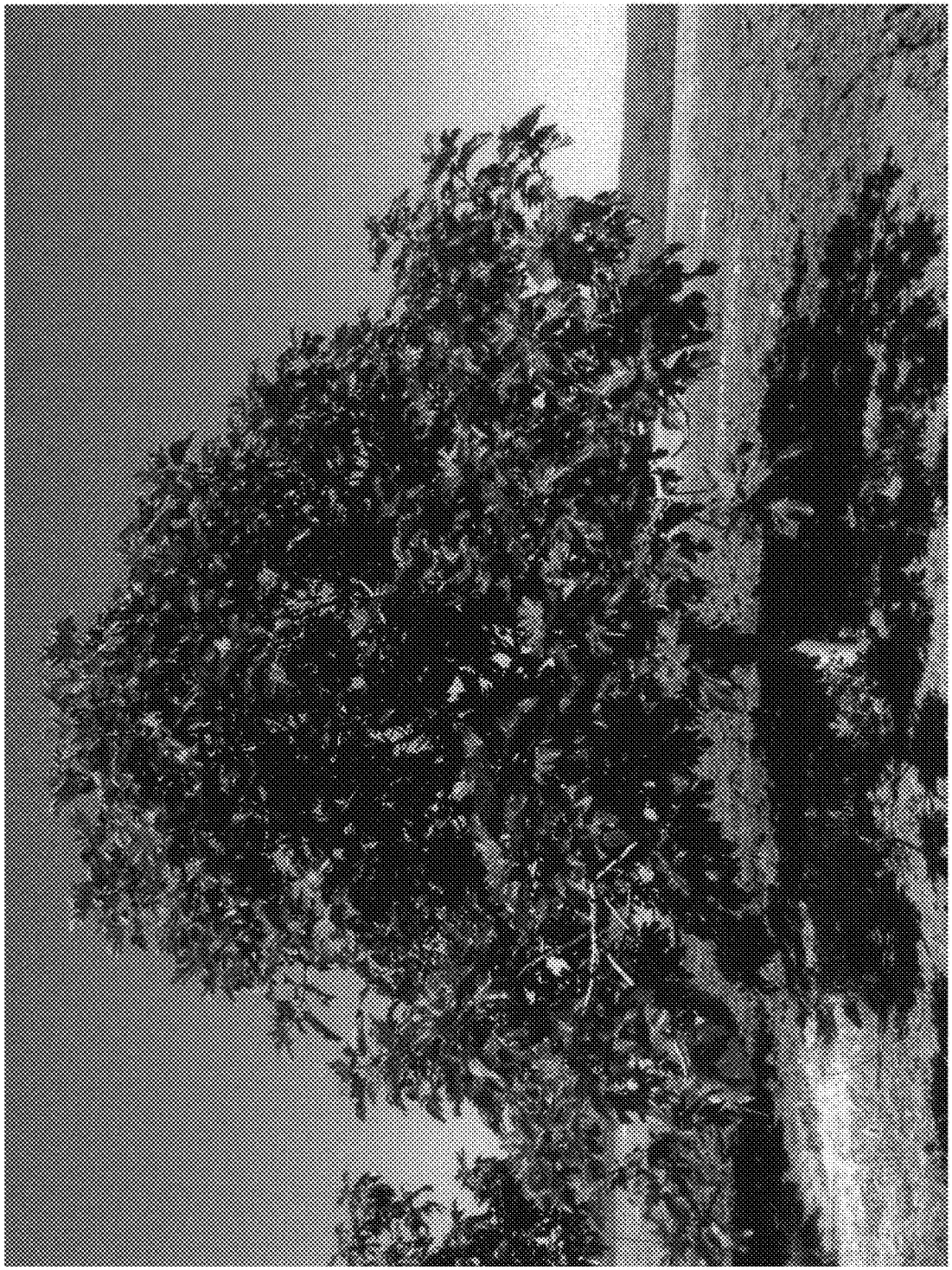
FIG. 1 is a photograph of the original '4-19' seedling tree, aged seven years.
Figure 2:
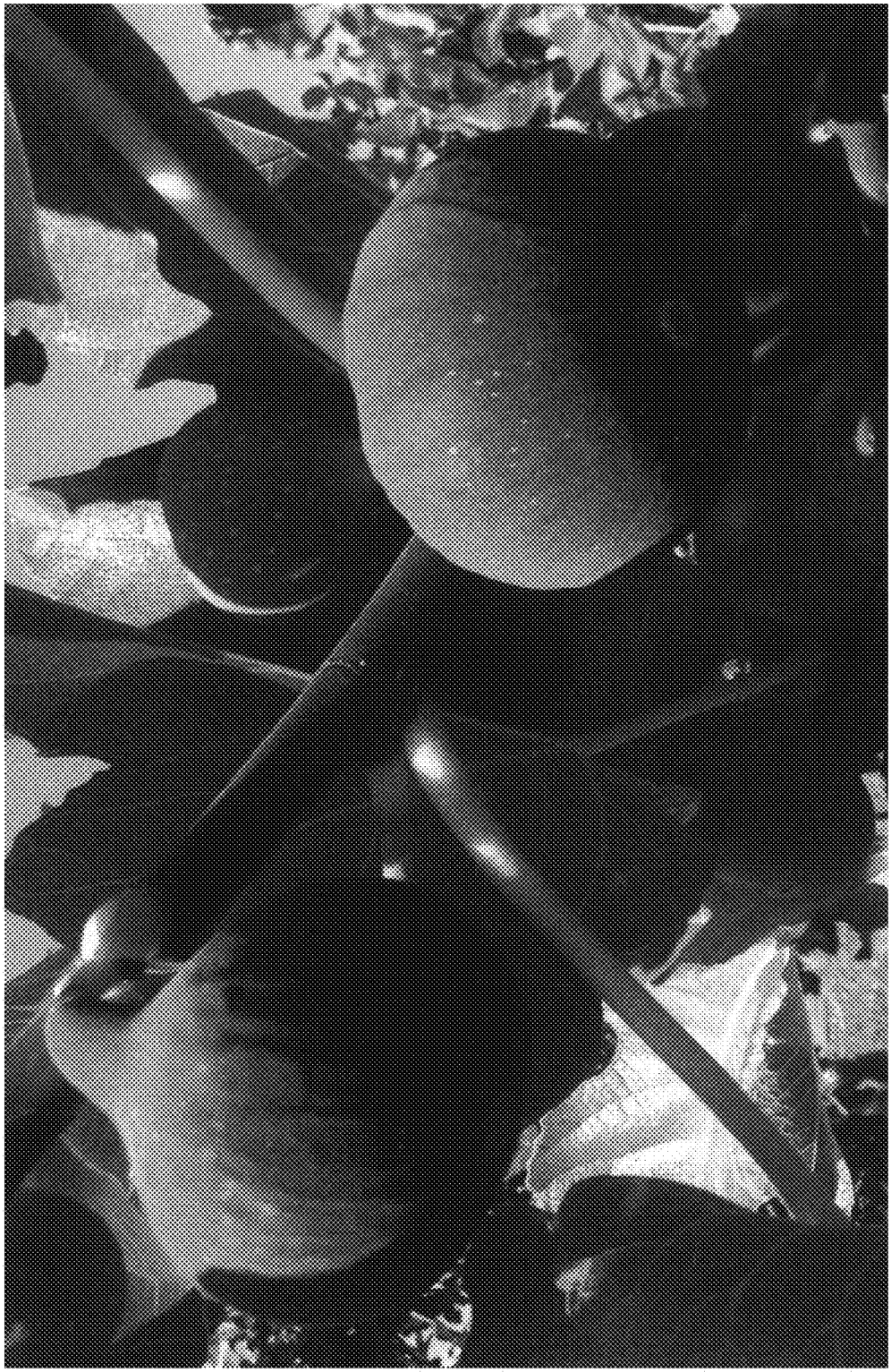
FIG. 2 is a photograph of fruit on the '4-19' tree.
Figure 3:
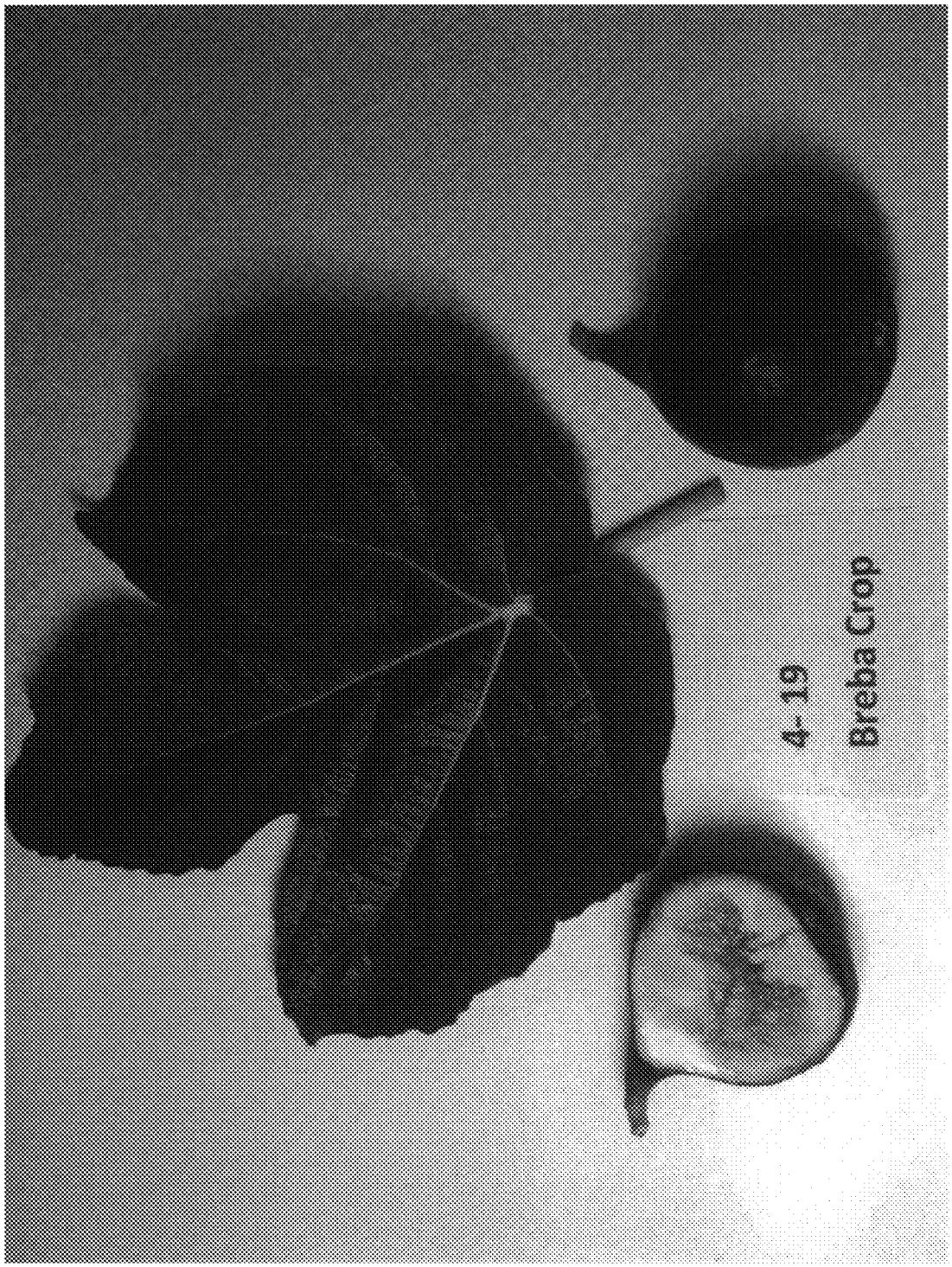
FIG. 3 is a photograph of a fruit and leaf of the first (breba) crop.
Figure 4:
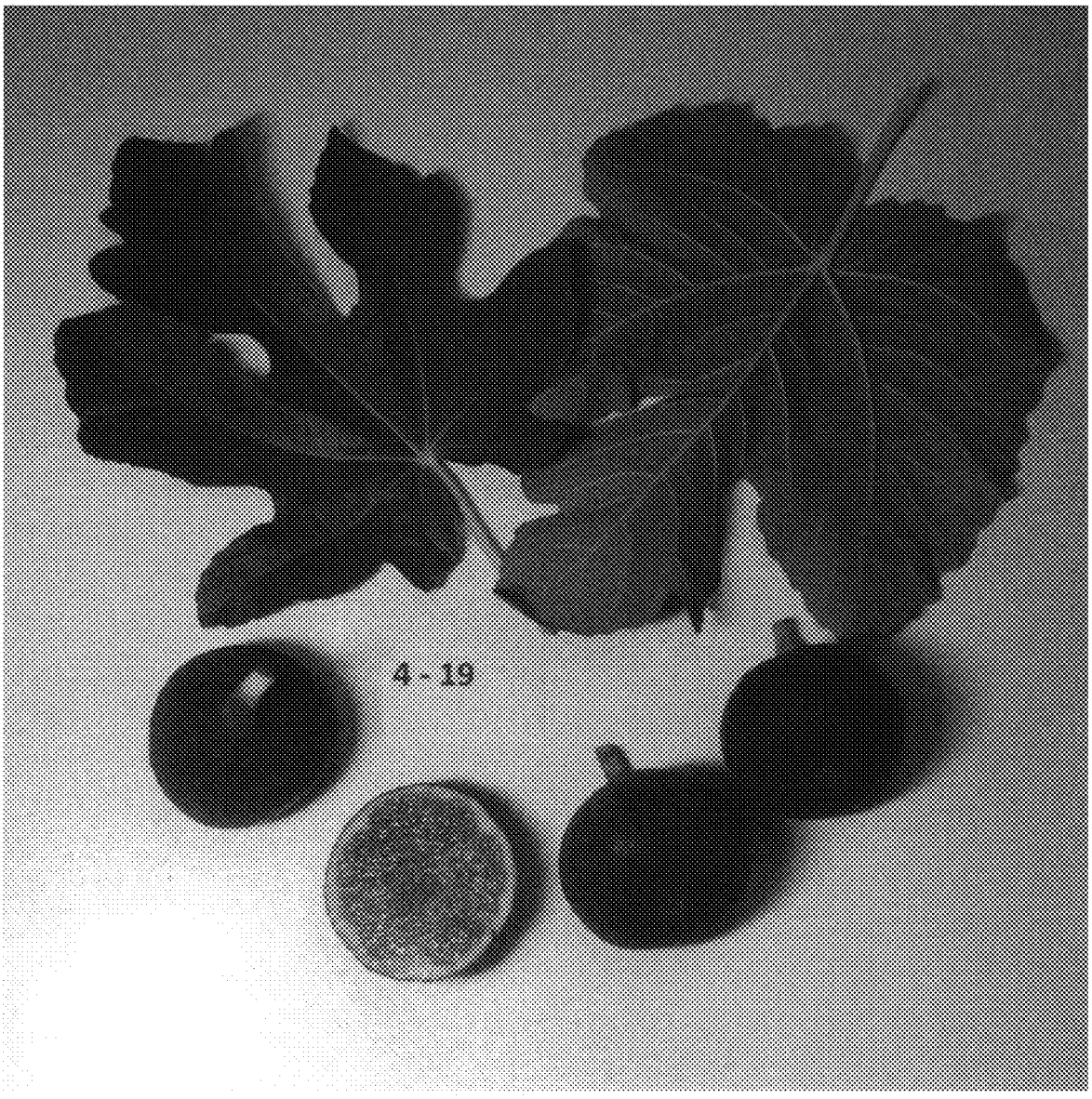
FIG. 4 is a photograph of fruits and leaves of the second (main) crop.

The following plant description was developed for the fig selection '4-19' during the 2019 growing season. Plant material and fruit was obtained from the original seedling tree of '4-19', growing in eastern Stanislaus County, Calif.

near the town of Waterford (hereinafter referred to as the "Waterford" location). The original '4-19' seedling tree is now in its eighth season, having been planted in early 2012. Color definitions that are utilized in this description are from The "Royal Horticultural Society Colour Chart", 3rd edition, published at London, GBR in 1995, except where general color terms of ordinary dictionary significance are used.

General description:

*Tree*.—This fig selection is a common fig, from the genus and species *Ficus carica*. The tree of '4-19' is large and vigorous for the species. It is upright-spreading in form with a round top and with moderately dense foliage. The selection has been hardy under typical San Joaquin Valley, Calif. climatic conditions. The tree has been very productive and has produced an abundant crop for several years. The subject tree is the original seedling tree, obtained from a seed of a hybrid cross made by the Inventor in 2011 in Roseville, Calif. The '4-19' fig was grown into a seedling tree at the Waterford location during the 2012 growing season. By 2019, the seedling tree had reached a height of approximately 15.5 to 16.0 feet (472 to 488 cm) and a width of approximately 20.5 to 23.0 feet (625 to 701 cm). The tree has only been slightly pruned after the first 2 to 3 formative years, with the exception of removal of low-hanging branches that interfered with cultural operations. Top growth extension in the 2019 growing season has varied from 7 to 18 inches (approximately 18 to 46 cm) in length. The original row spacing in this hybrid seedling planting was 12 feet (366 cm) between the rows and approximately 3 feet (91 cm) between the trees. At this point in time, due to the removal of discarded trees, there are only a few trees left standing in the block. The '4-19' fig is of the 'common' or 'persistent' type. This signifies that the selection does not need to be pollinated (caprified) by insects in order to set and mature fruit.

*Vigor*.—The tree has strong vigor.

*Trunk*.—The base of the tree trunk is 25 cm in diameter at a point that measures 10 cm up from the ground. The trunk color is gray, Fan 4 — Sheet 201D. The surface of the trunk has many fine, vertical striations and is covered with numerous small lenticels. The lenticels are variable in size and can range from 1 to 7 mm in length and from 0.5 to 2.0 mm in height. The lenticels usually have a flattened, oval form. The lenticels, at times, can be coalesced into bands across the trunk surface. The lenticels are usually darker in color than the trunk surface, varying from a dark gray, Fan 4 — Sheet 201A, to a somewhat lighter gray, Fan 4 — Sheet 201B. There is often callous present on the lenticel surface.

*Bark tubers*.—Three relatively small bark tubers are present below a point approximately 1.3 meters high on the main trunk. A first bark tuber is globose in form with a diameter of 1.0 cm and a height (i.e., thickness extending from the bark) of 0.9 cm. A second bark tuber is globose in form with a diameter of 0.8 cm and a height of 0.8 cm. A third bark tuber is oval in form with a length of 2.1 cm, a width of 1.7 cm, and a height of 1.3 cm. Color of the tubers is the same gray color as the color of the bark on the trunk, Fan 4 — Sheet 201D.

*Scaffolds*.—Multiple scaffolds arise from the main tree trunk. Scaffold diameters range from 2.8 to 4.75 cm, with six scaffolds present. The scaffold surfaces also have fine vertical striations and lenticels similar to the trunk of the '4-19' selection. The scaffold surface color is gray, Fan 4 — Sheet 201D.

*Branching density*.—The branching density of the tree is medium.

*Secondary branches*.—Many secondary branches arise from the primary branches of the '4-19' fig tree. These secondary branches are variable in size, ranging from 2.5 cm down to 1.6 cm in diameter and smaller. The larger secondary branches are similar in surface texture to the scaffolds, with striations and a few small lenticels. The basal portions of the older secondary branches are grayish in color, Fan 4 — Sheet 201D. Near mid-shoot on the secondary branches, the branch color is brown, Fan 4 — Sheet 200C, with some overtones of green, Fan 3 — Sheet 148A. In a transition zone from near mid-shoot to the tip of the secondary branches, the color of the bark is grayish-brown, Fan 4 — Sheet 199. A small amount of light, short and scattered pubescence can be present over the brownish areas.

*Shoots*.—Out near the tips of younger and smaller shoots, where the branch is still moderately soft and immature, the shoots are a lighter green color, Fan 3 — Sheet 144A. These younger shoots are pubescent with scattered short but stiff pubescence. Internode length of one-year-old vertical shoots is substantially variable, ranging from 6.7 to 7.3 cm near the base of the shoot and from 3.0 to 4.6 cm near the top of the shoot. Bud support swellings are absent in two-year-old shoots. Two-year-old shoots can vary in form from relatively straight for more vertical shoots, to somewhat curved upwards for more lateral shoots. Weeping of the secondary shoots is absent.

*Buds*.—The terminal buds on the shoots are usually conic in form with an attenuate tip. In dormant conditions, the length of the terminal bud ranges from 11 to 16 mm and the width of the terminal bud ranges from 5 to 6 mm. Terminal bud color at mid-season can be variable but is most frequently greenish-yellow, Fan 3 — Sheet 145A. The vertical angle of the tip of the terminal bud is most frequently slightly oblique to the end of the bearing branch.

*Leaf size and texture*.—The leaves of '4-19' are large in size and average, to somewhat above average, in thickness. The leaf measurements made were obtained from leaves growing at, or slightly below, mid-shoot on vigorous current season's growth. Leaf width varies from 20.5 to 23.5 cm, and leaf length varies from 24.0 to 28.0 cm, not including the petiole. The leaves are thick, slightly above average. Pubescence on the upper leaf surface is very short, stiff and somewhat scattered. Pubescence on the underside of the leaf is also short but soft and flexible. Pubescence on the underside leaf surface is found primarily on the surface of the leaf veins and is more dense than the pubescence found on the upper leaf surfaces. The upper surfaces of the '4-19' leaves are moderately glossy.

*Leaf form*.—Leaves found on a single individual tree can have some variability. Leaves on the '4-19' fig selection are palmately lobed and can possess three or five lobes. The lobes are most frequently latate in form and the leaf base is most frequently calcarate in form. The leaf sinuses are moderately deep, ranging from 4 to 7 cm in depth, most frequently averaging 6 cm in depth. There are mostly "U" shaped sinus bottoms but double "U" shaped forms can also be found. The leaf veins located on the lower leaf surface are very prominent. Veins located on the upper leaf surface are less prominent. Veins located on both the upper and lower surfaces are highly pubescent.

*Leaf margins*.—The leaf margins of the '4-19' selection are most frequently crenate in form but some variability can be present. There are usually crenations of medium size and uniformity, but large size and irregular crenations can often be found. At the outside base of some lobes there can be a few margin areas with a small number of serrations. The inner lobe margins within the leaf sinuses are usually linear in form, lacking serrations or crenations.

*Leaf and vein color*.—The upper leaf surface is a dark green color, ranging from a dark, Fan 3 — Sheet 137A, to a lighter green, Fan 3 — Sheet 137C. The lower leaf surface is a lighter green, Fan 3 — Sheet 139B. The leaf vein color can vary from a pale greenish, Fan 3 — Sheet 145B, to a more yellow-green, Fan 3 — Sheet 150C.

*Leaf petiole*.—The leaf petiole ranges from 7.0 to 11.2 cm in length. Thickness of the petiole varies from 0.5 to 0.8 cm in diameter, measured at the petiole base. The petiole surface is studded with scattered pubescence and is more dense where the petiole adjoins the base of the leaf blade. The petiole color is a light greenish-yellow, Fan 3 — Sheet 145A.

*Flowers*.—Many very small pedicellate fig flowers develop within each fig fruit, on the inner wall of the hollow fig receptacle known botanically as a "syconium". As each fruit initiates along the expanding shoot throughout the growing season, these syconia are entered, through the eye of the fruit, by the small fig wasp (*Blastophaga psenes* L.) The fig wasp has completed its life cycle inside a caprifig (see below) and is contaminated by pollen acquired from within the caprifig. The wasps enter and pollinate the fig flowers within the syconia as the syconia flowers become receptive when the syconia is about 1 to 2 cm in diameter. The florets have a five-part perianth and are unisexual, with either long-styled or short-styled pistillate flowers.

Description of the first and second crops: Descriptions of both the first and second crops of the new '4-19' fig selection are as follows. The first crop, also known as the "breba" crop, is produced on the previous season's growth. In general, this breba crop is usually lighter in volume than the second, or main, crop and the breba fruit is often larger than the fruit of the second crop. Depending on environmental factors, fruit size and quality and the crop volume of the breba crop may vary substantially from year to year. There can be from a month or more in difference between the first maturity dates for the breba and the second crop. The second crop is produced on current season's growth. This main crop is most frequently higher in production than the breba crop and makes up the bulk of commercial production for the variety. Fruit size is usually smaller in the main crop. Within any cultivar, there can be differences in appearance, color, flavor, size and other characteristics between the first and the second crop. Following are fruit descriptions for the breba and second crops of the new fig selection '4-19'.

First (breba) crop:

*Maturity*.—The '4-19' fig selection is of the "common" (persistent) botanical type. This fig type indicates that the fruit on the tree does not need pollination to set, either in the breba crop or in the second crop and to proceed to full ripe maturity. The date of maturity for the breba crop of the '4-19' fig selection began on Jun. 26, 2019 and continued until approximately Jul. 30, 2019.

*Size*.—The fruit size is large. Fruit width averages from 50 to 73 cm in diameter, and from 83 to 92 cm in length, not including the stem. Fruit weight can vary from 65 to 124 g per fruit during the early part of the season. Size and weight of the '4-19' breba fruit can decrease as the season progresses.

*Form*.—Form of the breba fruit is relatively spherical.

*Neck*.—The neck of the fruit on the breba crop is of medium length, ranging from 18 to 26 cm and is most often curved.

*Stalk*.—The fruit stalk is short, ranging from 6 to 9 mm in length and from 5 to 7 mm in diameter. Stalk color is green, Fan 3 — Sheet 144B. At times, the stalk color can be yellowish-green, Fan 3 — Sheet 151A, occurring on the upper surface where the stalk is exposed to sunlight. The stalk surface is covered with a short and very fine pubescence. Three bracts are often present on the stalk, appressed to the base of the fruit neck. The bracts range from 4 to 5 mm in height and from 5 to 6 mm in width, measured across the base of the bract. The bracts are roughly conic in form and usually brownish in color, Fan 4 — Sheet 177A, often with yellowish areas present, Fan 3 — Sheet 151C, and occasionally with purple striping, Fan 4 — Sheet 180B. The attachment of the stalk to the bearing branch is strong.

*Ribs*.—Low ribbing can be present on the fruit skin surface longitudinally, extending fully from the fruit neck to the fruit eye. These ribs are not prominent. Before full fruit maturity, the ribs appear darker than the surrounding body of the fruit. At full maturity, however, the body of the fruit and the fruit ribs blend into a uniform dark purple color, Fan 4 — Sheet 187A.

*Eye*.—The fruit eye is small in size and tight, averaging from 1 to 3 mm in diameter. The entrance to the fig ostiole is blocked by numerous overlapping scales, effectively restricting entrance by insects. Scale coloration is essentially the same color as the fruit body at maturity, Fan 4 — Sheet 187A.

*Skin*.—The fruit skin is of medium thickness, and quite durable. The skin surface is moderately glossy. There is an abundance of short and fine pubescence present over the surface of the fruit. This pubescence is so fine as to be hardly noticeable. Skin tears or renting are not usually present.

*Skin color*.—The skin color of the '4-19' fig is a very dark purple, Fan 4 — Sheet 187A, over much of the fruit surface. There is some lighter purple coloration on some fruit on the basal area of the fruit neck, progressing toward the stem, Fan 4 — Sheet 187C.

Where the fruit neck adjoins the fruit stem, a small amount of yellow-green coloration, Fan 3 — Sheet 145A, can be present on the end of the neck. This yellow-green ground color is not visible on many fruit once the fruit has reached full maturity.

*Skin flecking*.—Skin flecking can occur on most mature fruit of the '4-19' fig selection. Quantity of flecks can vary from very few to many. The flecks are most commonly found over the fruit shoulders up near the fruit neck, and can progress down to about mid-fruit and sometimes lower. Fleck size is quite variable, from 0.5 to 3.5 mm in height (measured longitudinally) and from 0.5 to 1.5 mm in width. The flecking is light colored and variable, from a cream color, Fan 4 — Sheet 158B, to an uneven pinkish coloration, Fan 1 — Sheet 36A.

*Meat*.—The fig meat is moderately thin along the lateral sides of the '4-19' fruit, from 3.0 to 6.0 mm at the thinnest point laterally and from 8.0 to 10.0 mm at the thickest points. The thickest areas of meat are at the stem end and basally. The meat thickness in these areas can range from approximately 8 to 18 mm, and can be irregular in distribution. The meat is tender and relatively sweet in flavor. Meat color can range from nearly white, Fan 4 — Sheet 155B, at the stem end to pinkish, Fan 2 — Sheet 75C, especially laterally.

*Pulp*.—The pulp of the '4-19' fig fruit usually fills the center of the fruit, with numerous irregular seams of pulp running through the interior. The seams are light reddish in color, Fan 1 — Sheet 37B, to a darker red, Fan 1 — Sheet 37A. Most of the fruit seeds are found within these seams. Light colored pulp occurs between the seams, and ranges in color between light pink, Fan 1 — Sheet 36B, to a lighter shade of pink, Fan 1 — Sheet 36D to almost white.

*Seeds*.—Numerous seeds are present in the pulp of the breba fruit crop. The amount of seeds varies, from between about 50 and about 1,600 seeds, with more seeds being present when more pollen-bearing wasps enter the fruit. This seed is quite small and can vary from oval to globose in shape. The seed diameter averages approximately 1.0 mm. Seed color is a light tan-brown, Fan 4 — Sheet 164C.

*Flavor*.—The fig fruit flavor is mild, sweet and pleasant.

*Usage*.—The primary usage of the breba crop of the '4-19' fig is for the fresh market.

*Internal cavity*.—The internal cavity of the fruit varies from absent to small.

*Lenticel density*.—The density of the lenticels is medium.

Second (main) crop: The second crop size in 2019 was about average. The second crop was borne on current season's growth. This description was developed during the last week of August, 2019. Fruit maturation range at this time varied from fully immature to fully tree ripe. The second crop of the '4-19' fig is classified as of the common or persistent type. It does not need to be pollinated (caprified) in order to set fruit that will develop into a mature fruit.

*Maturity*.—The second crop fruit of the '4-19' fig began to mature approximately around Aug. 15, 2019. The 2019 season was approximately 10 days to 2 weeks later than average. Figs are produced successively in axils of actively growing shoots from about late July until October in the San Joaquin Valley of California. The commercial production of figs terminates when the bearing shoot stops elongating, often due to heat or drought, or when climatic conditions such as fog, rain or frost, etc. makes the fruit unsalable.

*Size*.—The fruit is large in size and abundant. Fruit length, not including the stem, varies from 54 to 68 mm. Fruit width varies from 52 to 75 mm. Weight of the fruit can range from 64 to 156 g, with a high percentage of the early second crop in the 80 to 90 g range.

*Form*.—The second crop fruit form is most frequently oblate.

*Neck*.—The neck is usually short and moderately narrow. The neck diameter, where it joins the main body of the fruit, ranges from 10 to 14 mm. The neck is moderately curved. The neck length ranges from 9 to 19 mm, not including the stem.

*Stalk*.—The stalk of the '4-19' second crop fruit is relatively short. Stalk length can range from 5 to 12 mm and stalk width, measured basally, can range from 6 to 7 mm in diameter. Stalk color is variable, from a green-yellow, Fan 3 — Sheet 144C, to a more yellow-green, Fan 3 — Sheet 154A. The stalk surface is pubescent, with numerous short and fine hairs. Three conic-shaped bracts, from 4 to 5 mm wide basally, can be appressed to the fruit neck or, in many cases, the bracts are loose or flaring out from the top of the fruit neck. At full maturity, the bracts can be variable in coloration. Color can range from yellowish, Fan 3 — Sheet 151D, with purplish margins basally or, at times, purple striping along the entire bract margin, Fan 4 — Sheet 181B. With advanced maturity, the bracts are more entirely purplish in color, Fan 4 — Sheet 181B and C. The attachment of the stalk to the bearing branch is strong.

*Ribs*.—Skin ribbing is usually present on the '4-19' fruit surface in a longitudinal direction from the fruit neck down to the fruit eye. These ribs are low and not very prominent. Before maturity, the color of the ribs is darker than the surrounding fruit skin coloration. At maturity, however, the color of the fruit ribs blends well with the surrounding skin color of the fruit, which is a uniform dark purple color, Fan 2 — Sheet 79A.

*Eye*.—The fruit eye is small and tight, ranging from 1.5 mm to 2.0 mm in diameter. The fruit ostiole is blocked by many overlapping scales that restrict entrance into the fruit center by insects. The scales are roughly conic in form, with the scale color roughly the same as the skin color, Fan 2 — Sheet 79A. The purple coloration is somewhat lighter along the scale margins, Fan 2 — Sheet 78B.

*Skin*.—The fruit skin is of medium thickness and quite durable. The skin surface is only slightly glossy and is covered with a grayish bloom. There is also an abundance of short and fine pubescence present on the surface of the skin. The presence of this very fine pubescence is not very noticeable. Longitudinal skin renting occasionally occurs on the fruit lateral surfaces. This renting can be enhanced negatively by over-watering during the second crop harvest season.

*Skin color*.—The skin color of the second '4-19' crop fruit is a very dark purple, Fan 2 — Sheet 79A, over most of the fruit skin surface. There can be some lighter purple coloration, Fan 4 — Sheet 187B, around the basal area of the neck, and on the fruit neck itself. Occasional small areas of green-yellow ground color, Fan 3 — Sheet 148B, can be seen on the upper shoulder area of the fruit.

*Skin flecking*.—Skin flecking occurs on most mature fruit of the '4-19' fig. Fleck density can range from only a few to several dozen. The flecks are generally found laterally on the fruit, more dense over the fruit shoulders and up on the fruit neck. Size of the flecks varies substantially, from 0.5 mm up to as long as 3.5 mm in the longitudinal direction, and from 0.5 to 1.5 mm in width. The flecks are light and variable in color, from a cream color, Fan 4 — Sheet 158B, to an uneven pink color, Fan 1 — Sheet 36A.

*Fig meat*.—The fig meat occurs just under the skin of the fig fruit. It is moderately thin along the lateral sides of the fruit, from 3.0 to 6.0 mm at the thinnest point laterally, and from 5.0 to 12.0 mm at the thickest point. The stem end and the basal end of the fruit have the thickest areas of meat under the skin and can range from about 8.0 to 18.0 mm in thickness in those areas. The meat is tender and sweet in flavor. Color of the meat can vary from nearly white, Fan 4 — Sheet 155B, at the stem end, to, at times, slightly pink, Fan 2 — Sheet 75C, especially laterally.

*Fig pulp*.—The pulp of the second '4-19' fig crop usually completely fills the center of the fig fruit. At other times, numerous irregular seams of pulp interspersed with fig meat fills the center. The pulp color can vary from a light red, Fan 1 — Sheet 39A, to a darker red, Fan 1 — Sheet 42A. Many white fibers, Fan 4 — Sheet 155D, are visible within the pulp. Most of the fig seeds within the fruit are found within the pulp.

*Fig seeds*.—Numerous seeds are present in the pulp of the second '4-19' fig crop. The amount of seeds varies, from between about 50 and about 1,600 seeds, with more seeds being present when more pollen-bearing wasps enter the fruit. This seed is quite small and varies from oval to ovate in shape. The seed averages about 1.0 mm in diameter. Seed color is a light tan-brown, Fan 4 — Sheet 164B.

*Flavor*.—The fruit flavor is very good. It is sweet, rich and pleasant.

*Usage*.—The primary usage of the second '4-19' fig crop is for sale in the fresh market.

*Internal cavity*.—The internal cavity of the fruit is absent.

*Lenticel density*.—The density of the lenticels is medium.

COMPARISONS WITH THE PARENT PLANTS AND A KNOWN VARIETY

The 'SSB-121' fig is the female parent of the '4-19' fig. Although similar in appearance, the two figs are of a different horticultural classification. 'SSB-121' is a Smyrna non-persistent type fig. That means it needs to be caprified (i.e., pollinated) by the fig wasp in order to set and mature fruit. Without this caprification, the fruit of 'SSB-121' will start to grow, but quickly shrivel up and drop off the tree. In comparison, '4-19' is a common (persistent) type fig. That means it does not need pollination by the fig wasp in order to set and mature a full crop. The 'G-88' fig is the male (i.e., pollinator) parent of '4-19', known as a caprifig. It is also in a different horticultural classification than '4-19'. The 'G-88' fig is a male and contains anthers that will shed pollen when mature. The '4-19' fig is an edible fig and has no male parts or pollen within the interior of the fruit.

The '4-19' fig can be compared to the California Brown Turkey fig, one of the primary fresh market figs grown commercially in California. Both '4-19' and the California Brown Turkey are purple-skinned figs. '4-19', however, is a darker purple color and does not have any substantial yellow ground color showing around the fruit shoulders and neck as is the case with the California Brown Turkey. The second crop fruit of '4-19' may hold its size later in the season than fruit of the California Brown Turkey. The interior pulp of '4-19' may fill the center of the fruit completely, whereas the interior of the California Brown Turkey fruit is not completely filled. The fruit eye of '4-19' may be smaller than that of the California Brown Turkey. The precocity of the '4-19' tree closely resembles the precocity of the Mission fig variety (another purple-skinned cultivar also widely grown in California), whereas the precocity of the California Brown Turkey is greater.

What is claimed is:

1. A new and distinct cultivar of *Ficus carica* tree named '4-19', substantially as illustrated and described herein.

* * * * *